(12) United States Patent
Andrulitis

(10) Patent No.: US 6,319,231 B1
(45) Date of Patent: Nov. 20, 2001

(54) MEDICAL CONNECTOR

(75) Inventor: William B. Andrulitis, Haverhill, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/248,970

(22) Filed: Feb. 12, 1999

(51) Int. Cl.$^7$ ................................................... A61M 5/32
(52) U.S. Cl. .............................................. 604/175; 623/3.26
(58) Field of Search ..................................... 604/174, 175, 604/178, 179, 28, 500, 502, 8, 890.1, 891.1, 892.1, 7, 9, 10; 623/3.1, 3.26

(56) References Cited

U.S. PATENT DOCUMENTS

| | | | |
|---|---|---|---|
| 3,876,234 | 4/1975 | Harms | 285/38 |
| 3,919,722 | 11/1975 | Harmison | 3/1.7 |
| 4,138,148 * | 2/1979 | Zaremba | 285/317 |
| 4,222,127 | 9/1980 | Donachy et al. | 3/1.7 |
| 4,240,409 | 12/1980 | Robinson et al. | 128/1 D |
| 4,296,949 | 10/1981 | Muetterties et al. | 285/18 |
| 4,546,759 | 10/1985 | Solar | 128/1 D |
| 4,639,019 | 1/1987 | Mittleman | 285/332 |
| 4,650,486 * | 3/1987 | Chareire | 623/3 |
| 4,668,217 * | 5/1987 | Isono . | |
| 4,704,120 | 11/1987 | Slonina | 623/3 |
| 4,826,477 | 5/1989 | Adams | 604/4 |
| 4,981,484 | 1/1991 | Holfert et al. | 623/3 |
| 5,084,064 | 1/1992 | Barak et al. | 623/1 |
| 5,089,014 | 2/1992 | Holfert | 623/2 |
| 5,314,469 | 5/1994 | Gao | 623/3 |
| 5,776,116 | 7/1998 | Lopez et al. | 604/283 |

FOREIGN PATENT DOCUMENTS 0143517   6/1985   (EP) ................................. A61M/5/00

OTHER PUBLICATIONS

Holfert, J., et al., "A New Connector System for Total Artificial Hearts" (1987) *ASAIO*, vol. 10, No. 3; 151–156.

Pae, W., et al., "A Solution to Inlet Pannus Formation in the Pneumatic Artificial Heart" (1985) *Trans. Am. Soc. Artif. Intern. Organs*, vol. XXXI; 12–16.

* cited by examiner

*Primary Examiner*—Sharon Kennedy
*Assistant Examiner*—Catherine Serke
(74) *Attorney, Agent, or Firm*—Nutter, McClennen & Fish LLP

(57) ABSTRACT

A medical connector for connecting a cardiac assist device to vascular tissue includes a base connector adapted to be attached to the cardiac assist device and a vascular tissue connector adapted to be attached to the vascular tissue. A retaining ring holds the base connector to the vascular tissue connector. The medical connector also includes an alignment feature and an engagement feature, each defined by a portion of either the base connector or the vascular tissue connector and a portion of the retaining ring. The alignment feature causes the vascular tissue connector to axially self-align with the base connector. The engagement feature causes the retaining ring to move first into a biased position and then to snap into engagement when the vascular tissue connector attaches to the base connector in an axially-oriented motion.

82 Claims, 6 Drawing Sheets

MEDICAL CONNECTOR

BACKGROUND OF THE INVENTION

1. Field of the Invention

This invention relates to generally to medical connectors for fluid transport and, more particularly to, connectors for use with implantable medical devices, such as cardiac assist devices.

2. Related Art

Cardiac assist devices are connected to a patient's vascular system to aid in or completely replace the function of pumping blood throughout a patient's body. Development of cardiac assist devices progressed from relatively bulky and intrusive external devices to completely implantable devices. In these devices, a typical connection between vascular tissue and the cardiac assist device includes a connector having a first half sutured onto the vascular tissue and a second half attached to the cardiac assist device. To join the two halves, conventional connectors typically employ a twisting engagement wherein the connector halves must first be aligned then rotated relative to each other.

Certain disadvantages with these twist-type connectors exist. For example, the mating halves may be difficult to align, resulting in a time-consuming and laborious procedure during surgery. In addition, when using an implantable cardiac assist device, the presence of blood and other fluids in the depth of a poorly visible and severely cramped surgical field results in limited maneuverability of a surgeon's hands, thereby increasing the difficulty in firmly grasping and joining the connector halves and subsequently imparting the rotative action. Further, the rotative action required for engagement of the twist-type connector may damage or twist the vascular tissue to which one half of the connector is attached or damaging the surrounding tissue. Another disadvantage with twist-type connectors is that they can come apart.

Another type of connector, such as that disclosed in U.S. Pat. No. 4,650,486, which attempts to alleviate some of the disadvantages with the twist-type connector, includes two cooperating connector halves, one attached to the cardiac assist device and the other attached to the end of the vascular tissue. The connector halves are attached to each other by sliding one half in a plane relative to the other, with the plane being substantially orthogonal to blood flow.

The disadvantage of this approach when using implantable devices is that the sliding action requires much more space than may be available in the cramped surgical field. For example, to slide such a connector half relative to the other necessarily requires that the space that must be available should be about twice the amount of space as compared to the space required for the final connection. A further drawback to this technique is that the tissue surrounding the connector site may get caught between the two connector halves as they slide relative to each other.

SUMMARY OF THE INVENTION

The present invention is a medical connector for connecting vascular tissue to a medical device that overcomes the above and other disadvantages of conventional connectors. The connector includes one half adapted for attachment to the medical device and another half adapted for attachment to the vascular tissue. The two halves cooperate with each other so as to be self-aligning when moved in an axial direction. Further movement in the axial direction causes the two halves to lock together.

In one particular aspect of the invention, a medical connector for connecting vascular tissue to a medical device is disclosed. The connector includes a base connector adapted to be attached to the medical device; and, a vascular tissue connector adapted to be attached to the vascular tissue. The base connector and the vascular tissue connector cooperate with each other so as to cause each connector to axially align relative to each other when initially brought into contact with each other and engage each other when moved in opposite, axially oriented, directions toward each other. Thus, connection can be easily completed without detailed visualization of the connector in the confined space of the surgical field.

In another aspect of the invention, a medical connector for connecting vascular tissue to a medical device is disclosed. The medical connector includes a first connector half having a retaining ring having a rest position and a biased position and a second connector half having a retaining ring groove formed therein. An alignment feature and an engagement feature, each defined by a portion of said connectors and a portion of said retaining ring, causes the first connector to axially self-align with the second connector and causes the retaining ring to move first into the biased position and then to snap into engagement within the retaining ring groove.

In another aspect of the invention, a medical connector for connecting vascular tissue to a medical device is disclosed. The connector includes a base connector, defining an axis, adapted to be attached to the medical device and a vascular tissue connector, also defining an axis, adapted to be attached to the vascular tissue. A retaining ring having a rest position and a biased position is housed within either the vascular tissue connector or the base connector. A retaining ring groove configured to engage with the retaining ring is formed on an outer circumference of the other connector. An alignment feature and an engagement feature each is defined by a portion of either the base connector or the vascular tissue connector and a portion of the retaining ring. The alignment feature causes the vascular tissue connector to axially self-align with the base connector. Thus, alignment can be easily completed without detailed visualization of the connector, making the present invention particularly beneficial in the confined space of the surgical field. The engagement feature causes the retaining ring to move first into the biased position and then to return at least partially toward the unbiased position so as to snap into engagement within the retaining ring groove when the vascular tissue connector attaches to the base connector in an axially oriented motion. The snap-engagement provides immediate tactile feedback to ensure a complete connection.

In one embodiment, the retaining ring includes a beveled edge. The beveled edge defines at least a portion of the alignment feature. Either the base connector or the vascular tissue connector includes a leading edge defining at least a portion of the alignment feature and includes a radiused edge and a chamfered portion conjoined with and extending away from the radiused edge.

In yet another embodiment either the vascular tissue connector or the base connector includes an annular body having an end face. The end face is completely continuous, thereby reducing tissue snagging when the vascular tissue connector is brought into proximity with the base connector. The annular body has an inner and outer surface. The inner surface has an annular groove formed therein for housing the retaining ring. The outer surface has an opening formed therein extending through to the annular groove of the inner surface to allow a portion of the retaining ring through the body so that the retaining ring can be moved to the biased position to facilitate removal of the vascular tissue connector from the base connector. In another embodiment, the base connector and the vascular tissue connector each have a body. Each body has a substantially minimal profile relative to the vascular tissue.

In still another embodiment, a plurality of o-ring seals are disposed at an interface between the base connector and the vascular tissue connector when connected theretogether. The interface defmes an o-ring seal groove for receiving the o-ring seals in a generally co-axial alignment. An o-ring seal may extend past the o-ring seal groove a predetermined distance, which may be defined by about one-half a diameter of the o-ring seal.

In yet another embodiment, the connector includes a plug connector adapted to be connected to the vascular tissue connector to test for leakage between the vascular tissue connector and the vascular tissue when the vascular tissue connector is attached to the vascular tissue. Leakage between the vascular tissue connector and the vascular tissue itself may also be determined with the use of the plug connector. The plug connector may also include a pressure port formed therein to pressurize the connection, also to determine leakage.

In another aspect of the invention, a method of attaching vascular tissue to a medical device utilizing a medical connector system is disclosed. The connector system has at least two connectors. Each connector includes a base connector defining an axis and being attached to the medical device and a vascular tissue connector defining an axis for attaching to the vascular tissue. A retaining ring is housed within either the vascular tissue connector or the base connector. The retaining ring has a rest position and a biased position. A retaining ring groove is formed on an outer circumference of either the base connector or the vascular tissue connector and is adapted to engage the retaining ring. A tissue connection member is housed within the vascular tissue connector. The connector system includes an alignment feature and an engagement feature each defined by a portion of either the base connector or the vascular tissue connector and a portion of the retaining ring. The method includes the steps of suturing a first tissue connection member, together with a first vascular tissue connector, to a first vascular tissue and positioning the medical device such that a first base connector aligns with the first vascular tissue connector to determine the required size of a second tissue connection member. The second tissue connection member is then conformed to the determined length. The method further includes the step of sewing the second tissue connection member to a second vascular tissue and positioning the medical device such that both base connectors align with both vascular tissue connectors, respectively. To complete the connection, each base connector is axially moved relative to each vascular tissue connector in an axial direction.

In one embodiment, the connector system further includes a plug connector. The method further includes the step of connecting the plug connector to the vascular tissue connector thereby plugging the vascular tissue; and, testing for leakage between the tissue connection member and the vascular tissue by either releasing a clamp from the vascular tissue to allow blood pressure to build in the vascular tissue connector or injecting a solution through a pressure port formed in the plug connector thereby causing pressure to build in the vascular tissue connector. Leakage between the sutures and the tissue connection member may also be detected. Thus, any blood leakage caused by the connection is remedied before completion of the surgery.

In yet another embodiment, the connector system further includes an installation tool for holding the vascular tissue connector. A removal tool may also be provided for removing either the vascular tissue connector or the plug connector.

Various embodiments of the present invention provide certain advantages and overcome certain drawbacks of the conventional techniques. Not all embodiments of the invention share the same advantages and those that do may not share them under all circumstances. This being said, the present invention provides numerous advantages only some of which are noted above.

Further features and advantages of the present invention as well as the structure and operation of various embodiments of the present invention are described in detail below with reference to the accompanying drawings. In the drawings, like reference numerals indicate identical or functionally similar elements. Additionally, the left-most one or two digits of a reference numeral identifies the drawing in which the reference numeral first appears.

BRIEF DESCRIPTION OF THE DRAWINGS

The invention will now be described, by way of example, with reference to the accompanying drawings, in which.

DETAILED DESCRIPTION

The medical connector system of the present invention is suitable for connecting vascular tissue to a medical device. The connector includes a first half connector half adapted to attach to the medical device and a second connector half adapted to be attached to the vascular tissue. The connector halves cooperate to be self-aligning and lock together when moved in initially brought into contact with each other and when moved in an opposite axial direction toward each other. Any possibility of misalignment is therefore reduced and the connection can thus be easily completed without detailed visualization of the connector in the confined space of the surgical field.

As used herein, the term "vascular" refers to any body passageway or tissue of a person's circulatory system, lymph system, gastrointestinal system, etc., for example. Accordingly, the vessels to which a connector half is attached may include arteries, veins, lymph ducts, intestines, urethra, heart muscle, etc.

Figure 1:
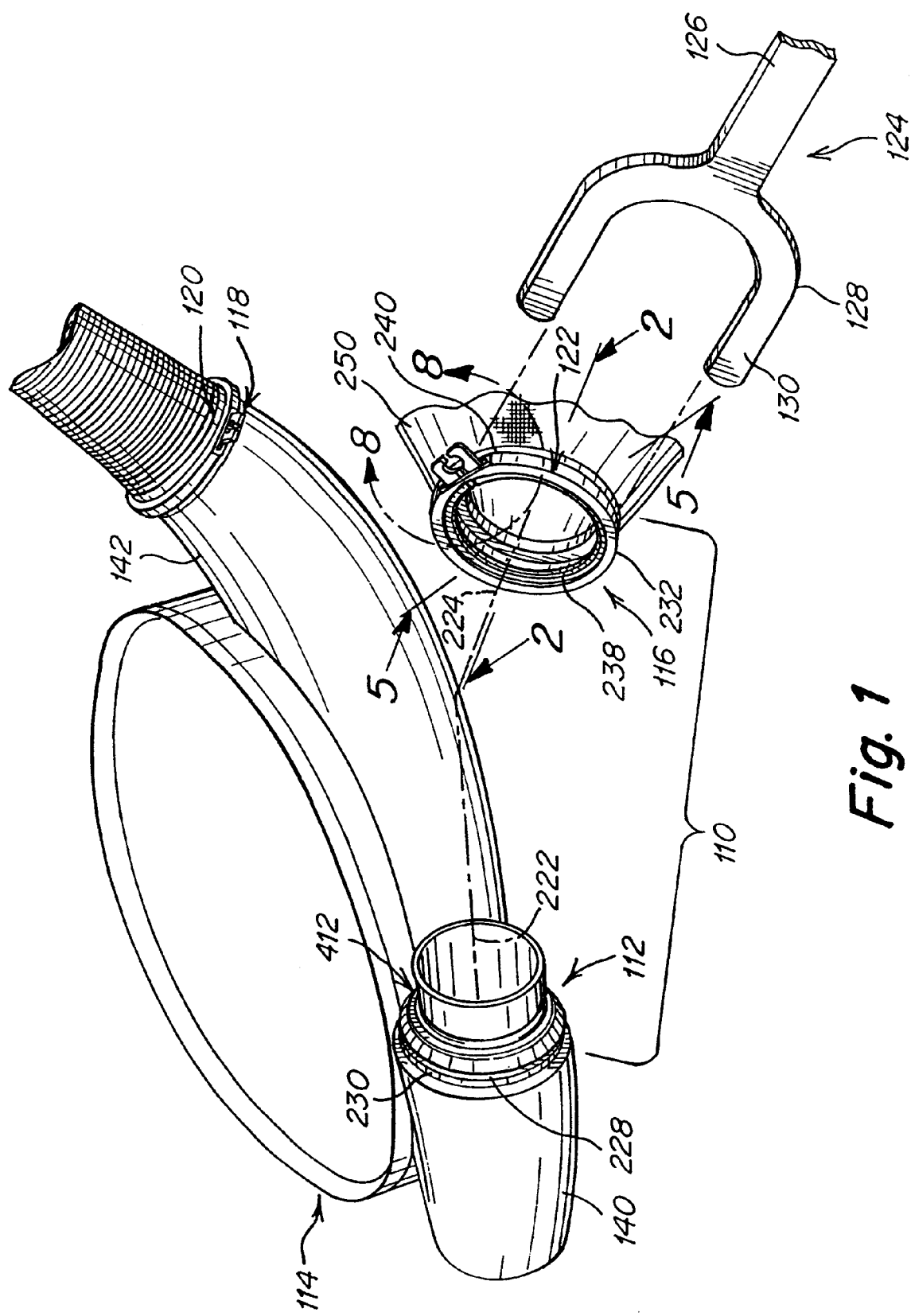
FIG. 1 is an exploded perspective view of one embodiment of the medical connector system for use in a cardiac assist device according to the present invention.
Figure 2:
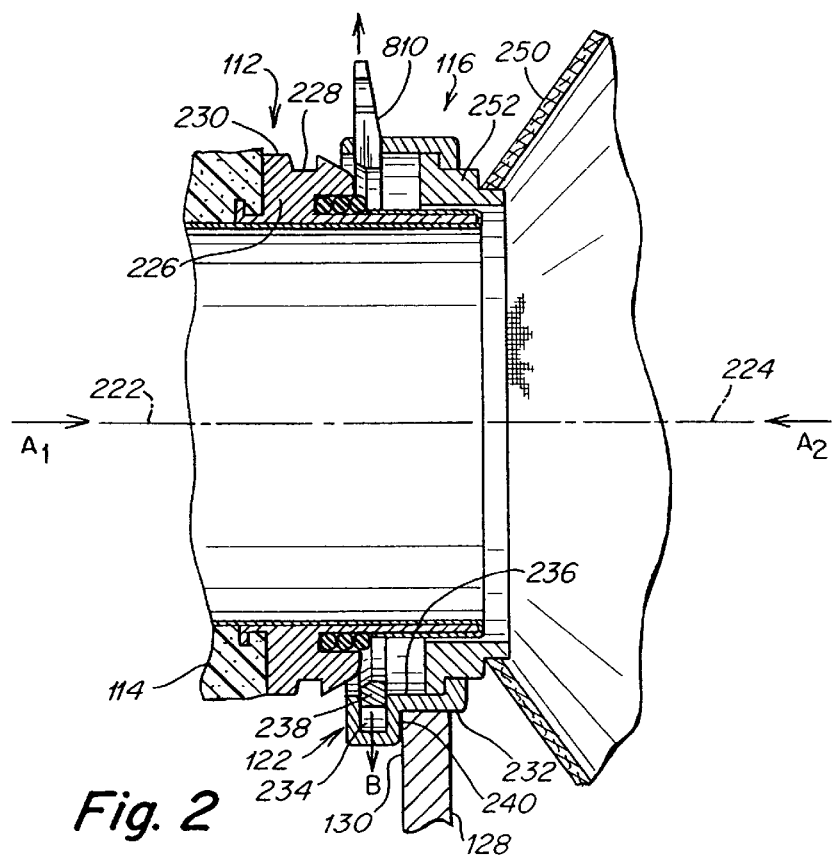
FIG. 2 is a cross-sectional view showing connection of the connector.
Figure 3:
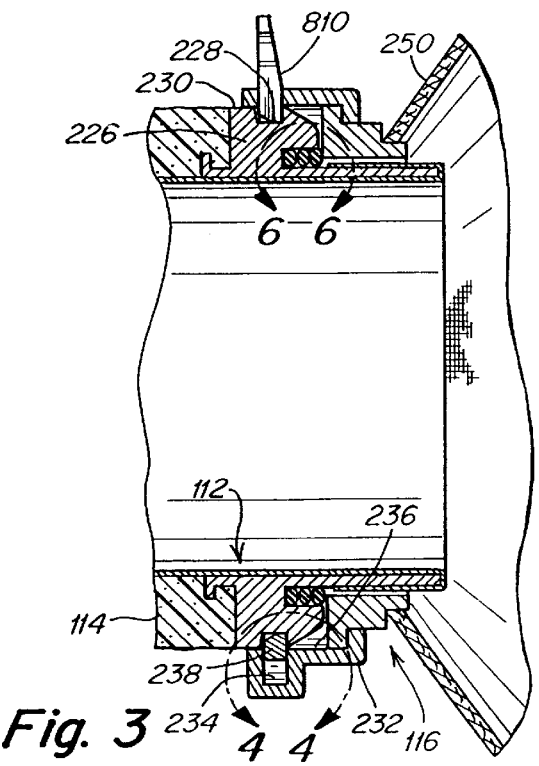
FIG. 3 is a cross-sectional view showing the connector in its connected configuration.

FIG. 1 is an exploded perspective view of one embodiment of the medical connector system 110. FIGS. 2 and 3 are cross-section views of the connector system 110 in an unengaged and engaged position, respectively. The medical connector system 110 includes a base connector 112 adapted to be attached to a medical device, such as a cardiac assist device 114 (only a portion of which is shown) and a vascular tissue connector 116 adapted to be connected to vascular tissue (not shown). A second base connector 118 and second vascular tissue connector 120 may be used to connect other portions of the cardiac assist device 110 with other areas of a patient's vascular tissue. Accordingly, the vascular tissue connectors 116, 118 are adapted to attach to the corresponding vascular tissue through the use of a tissue connection member, as will be fully explained hereinafter.

FIG. 2 is a cross-section of the base connector 112 and the vascular tissue connector 116 taken along line 2—2 of FIG. 1. The base connector 112 defines an axis 222 and the vascular tissue connector 116 defines an axis 224. The base connector 112 includes a body 226 and a retaining ring groove 228 formed on an outer surface 230 of the body 226. The vascular tissue connector 116 also includes a body 232 having an annular groove 234 formed on an inner surface 236 of the body 232. A retaining ring 238 is disposed within the annular groove 234 so as to be loosely contained therein for limited movement as will become apparent hereinafter.

To interlock the connector, the vascular tissue connector 116 is brought into rough alignment with base connector 112 such that the axes 222, 224 are substantially coincident. As the connectors are moved in opposite axial directions toward each other, labeled as directions "$A_1$" and "$A_2$" the retaining ring 238 may become substantially aligned with the base connector 112 and moves into a biased position (i.e., where the retaining ring 238 is opened circumferentially outward into the annular groove 234 to accommodate the outer diameter of the base connector 112), labeled as direction "B". Continued movement causes the retaining ring 238 to snap into engagement within the retaining ring groove 234, where the retaining ring 238 assumes a diameter smaller than the diameter assumed in the biased position, thereby interlocking the two halves. In a preferred embodiment, when retaining ring 238 is engaged within retaining ring groove 234, the retaining ring 238 remains in a slightly biased position.

Although the retaining ring 238 is shown and described as being disposed within the body 232 of the vascular tissue connector 116 and the retaining ring groove 228 is formed on the body 230 of the base connector 112, the inverse may be provided whereby the retaining ring may be disposed within the base connector 112 and the retaining ring groove may be formed on the vascular tissue connector 116. Also, although the retaining ring is shown and described as expanding circumferentially outward to move into the biased position so as to engage within an externally formed retaining ring groove, the connector may be constructed and arranged such that the retaining ring moves circumferentially inward to move into a biased position for engagement within an internally formed retaining ring groove.

Figure 4:
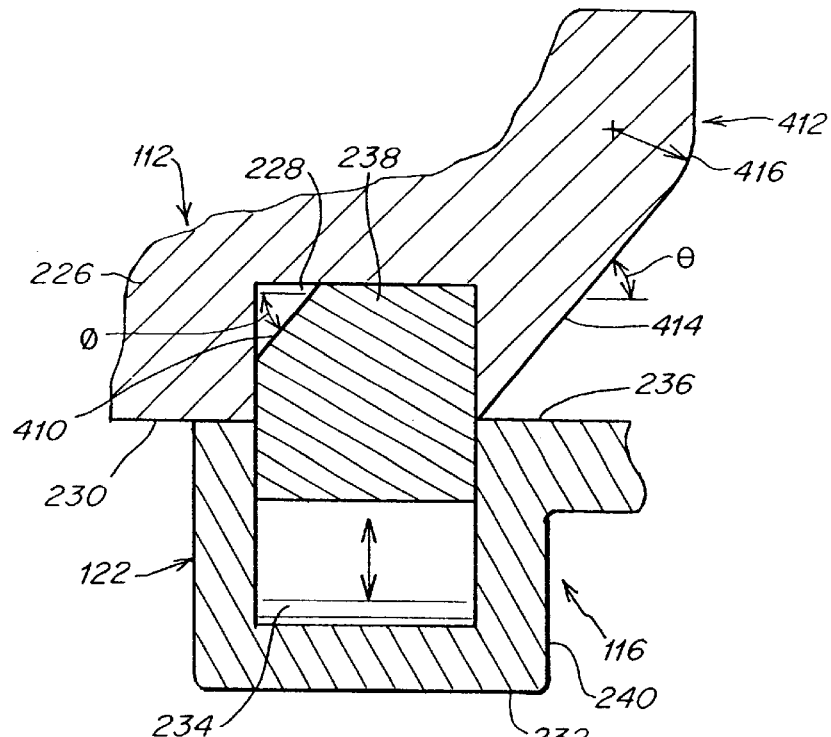
FIG. 4 is an enlarged view of a portion of the connector encircled by line 4 of FIG. 3.

FIG. 4 shows an enlarged view of portions of the retaining ring 238, body 230 of the base connector 112 and the body 232 of the vascular tissue connector 116 of one illustrative embodiment of the present invention. In this illustrative embodiment, the connectors 112, 116 include an engagement feature that includes a beveled edge 410 formed at an angle $\Phi$ cooperating with a leading edge 412 formed on body 230 of the base connector 112. The leading edge 412 includes a chamfered portion 414 formed at angle $\theta$, which complements the beveled edge 410 to facilitate biasing the retaining ring 238, for example, by causing the retaining ring 238 to expand within the annular groove 234. In a preferred embodiment, the angles $\Phi$ and $\theta$ are about 30°, although virtually any angle may be used that is suitable for the particular application and anticipated environment. Also, rather than providing an angle of the beveled edge and the chamfered portion, a radius, or any other geometric form that causes the retaining ring to move into a biased position when the connector halves are joined together may be provided.

Figure 5:
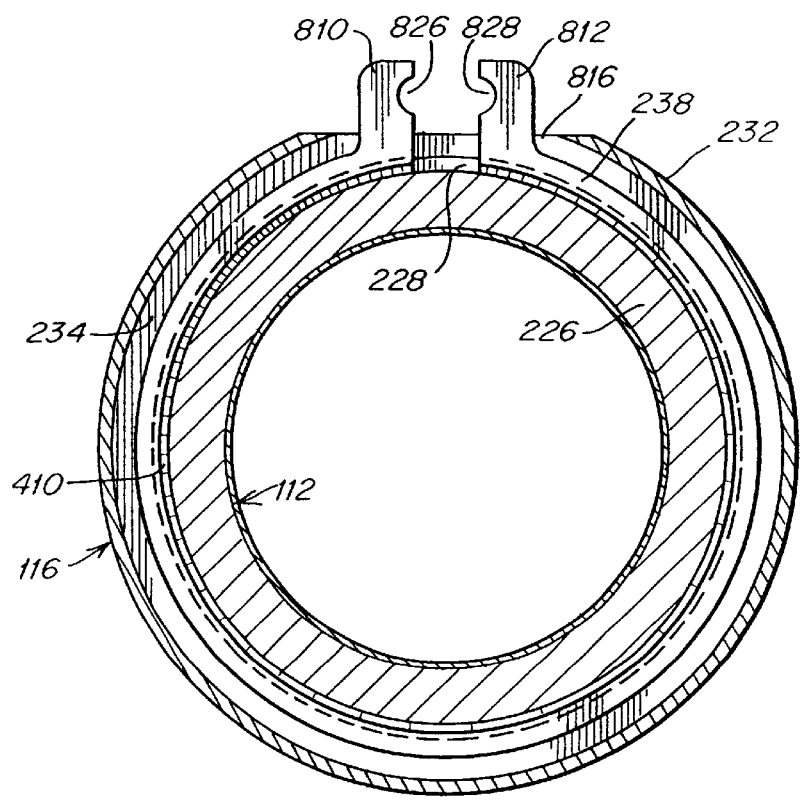
FIG. 5 is a full cross-sectional view of the connector of the present invention taken along line 5—5 of FIG. 1.

Continuing with reference to FIG. 4, the connectors may include an alignment feature wherein the leading edge 412 includes a radius 416 formed adjacent to the chamfered portion 414. When the vascular tissue connector 116 is initially brought into rough alignment with the base connector 112, the beveled edge 410 of the retaining ring 238 contacts the radius 416. The beveled edge 410 and the radius 416 cooperate to cause the retaining ring 238, and subsequently the vascular tissue connector 116, to substantially axially align with the base connector 112. Thus, the connector 110 is self-aligning According to the present invention, as best shown in FIG. 5, the body 232 of the vascular tissue connector 116 has a substantially minimal profile relative to the vascular tissue (not shown). The base connector 112 also has a minimal profile (see FIG. 1). These minimal profiles may be desirous so that minimal space is utilized within the body cavity of a patient.

Also according to the present invention, end face 122 (see FIG. 1) of the vascular tissue connector 116 may be completely continuous, meaning there are no openings formed therearound. Thus, the potential for tissue snagging as the vascular tissue connector 116 is brought into proximity with the base connector 112 is reduced. That is, because the end face 122 is completely continuous, there are no edges on which tissue may become caught.

To facilitate ease of connection between the base connector 112 and the vascular tissue connector 116, an installation tool 124, as shown in FIGS. 1 and 2 may be used. Thus, in another illustrative embodiment, the body 232 of vascular tissue connector 116 further includes end face 240. The installation tool 124 includes a handle 126 and a "U"-shaped holder 128 having a bearing surface 130. The vascular tissue connector 116 is captured by the holder 128 in a manner such that the end face 240 bears against the bearing surface 130. A surgeon or other medical professional holds the installation tool 124 to hold the vascular tissue connector 116 as the base connector 112 is connected thereto.

Figure 6:
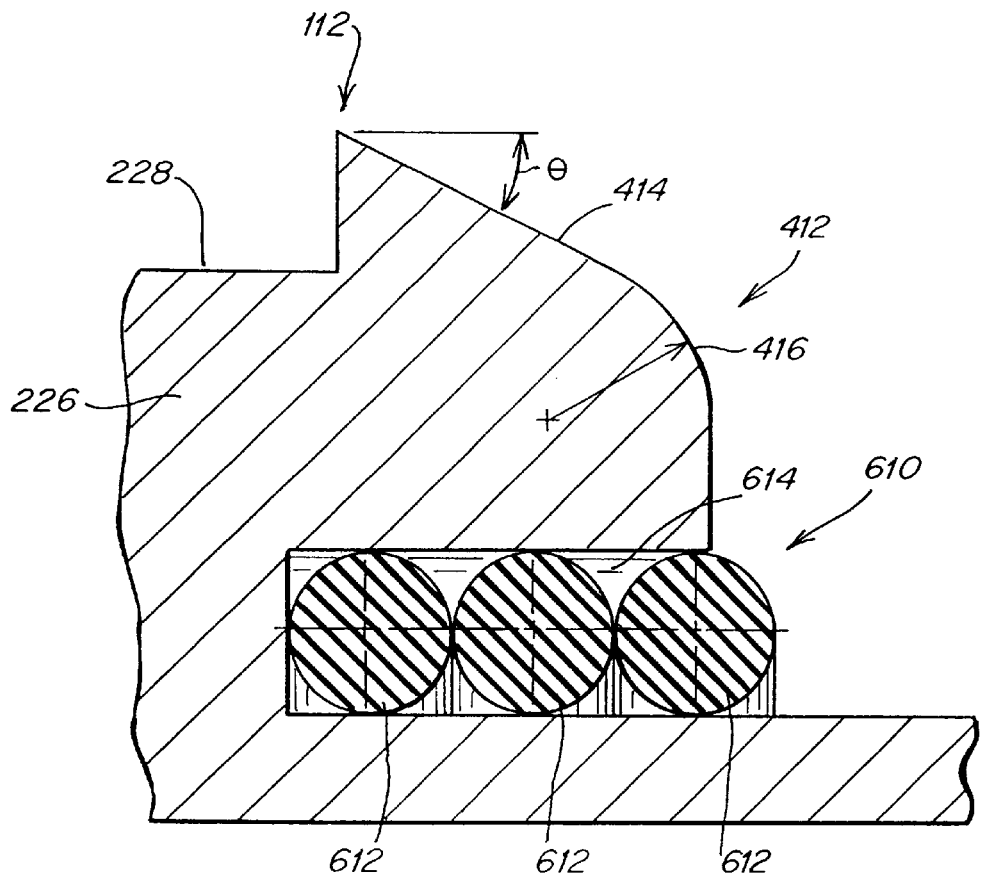
FIG. 6 is an enlarged view of a portion of the connector encircled by line 6 of FIG. 3.
Figure 7:
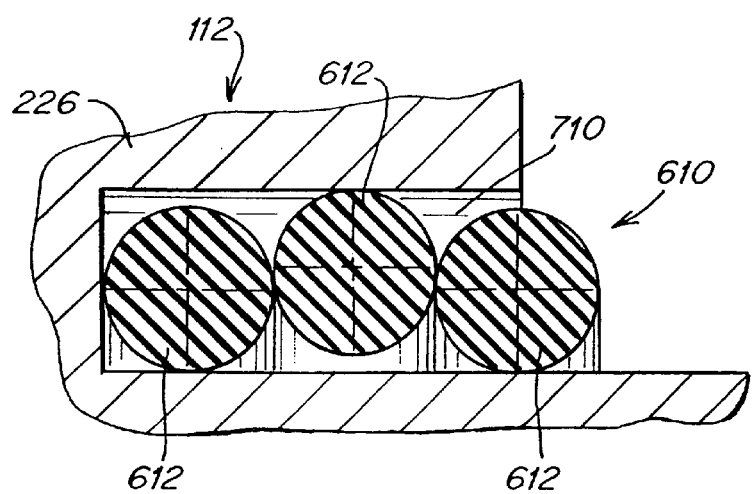
FIG. 7 is an illustrative embodiment of FIG. 6.

Turning now to FIGS. 6 and 7, which are enlarged views of an interface between the base connector 112 and the vascular tissue connector 116, another illustrative embodiment is shown. In this embodiment, the connector 110 includes a plurality of o-ring seals 612 disposed at an interface 610 between the base connector 112 and vascular tissue connector 116 (not shown in FIG. 6) when the two are connected together. The interface 610 includes an o-ring seal groove 614 for receiving the plurality of o-ring seals 612 in a substantially coaxial alignment. In the particular example shown, the o-ring seal groove 614 is formed in the base connector 112. However, the o-ring seal groove 614 alternatively may be formed in the vascular tissue connector 116. The o-ring seals 612 may extend past the o-ring seal groove 614 by a predetermined distance. In a preferred embodiment, a single o-ring seal extends beyond the o-ring seal groove 614 by a distance of about one-half diameter. However, the predetermined distance alternatively may depend on a number of factors including, but not limited to, the number of o-ring seals used, the size of the o-ring seals, the elasticity of the o-ring seals and other parameters known to those skilled in the art.

The use of a plurality of o-ring seals, such as the use of three o-ring seals, may allow for a greater range of linear travel of the vascular tissue connector 116 relative to the base connector 11, thereby increasing the spring force for biasing the base connector 112 away from the vascular tissue connector 116. This increased spring force acts as an increased normal force on the retaining ring 238 so as to further limit its rotation within the annular groove 234 as well as inhibit any inadvertent biasing of the retaining ring 238, which may otherwise cause the retaining ring 238 to disengage from the retaining ring groove 228.

The use of a plurality of o-ring seals further compensates for any misalignment between the individual o-ring seals 612 and the o-ring seal groove 614 due to, for example, tolerance build-up. For instance, if the o-ring seal groove is manufactured too large and only one o-ring seal is used, a leak path may be established. However, as shown in FIG. 7, given a plurality of the same size o-ring seals 612 and a groove 710 that is larger than desirable, the o-ring seals 612 will compress in a manner such that some of the seals will align with the inner wall of the groove 710 while the other seals 612 will align with the outer wall of the groove 710, thereby providing an effective seal.

Figure 8:
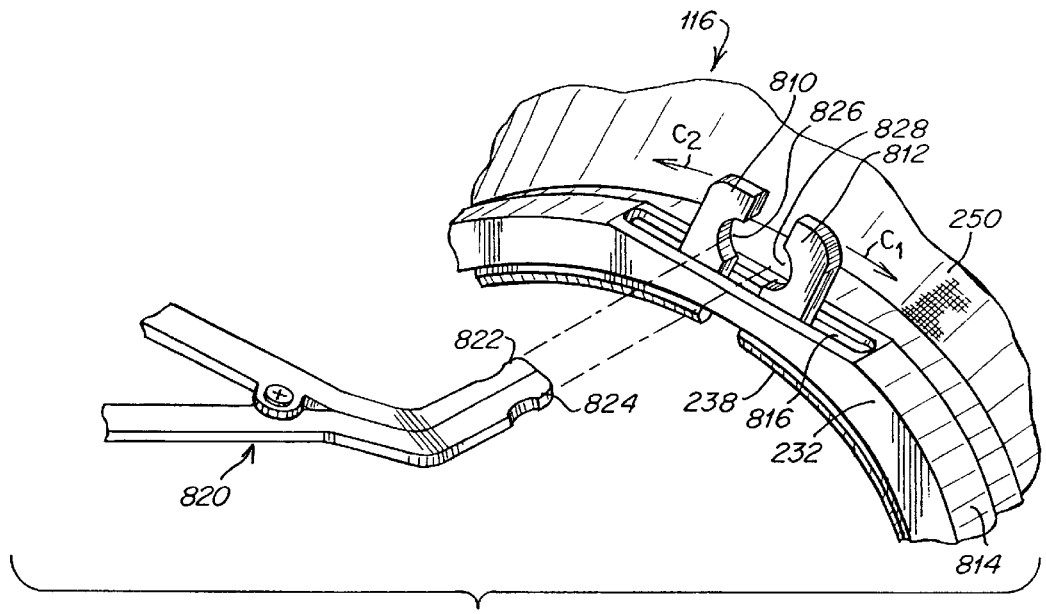
FIG. 8 is an enlarged view of a portion of the connector encircled by line 8 of FIG. 1.

FIG. 8 is an enlarged view of the area encircled by line 8 of FIG. 1. In this illustrative embodiment, the retaining ring 238 includes radially extending hooks 810, 812. The outer surface 814 of the body 232 of the vascular tissue connector 116 includes an opening 816 formed therein and extending through to the annular groove 234 of inner surface 236 to allow the hooks 810, 812 to extend therethrough. To remove the vascular tissue connector 116 from the base connector 112, if so desired, retaining ring 238 is moved into its biased position so that it will move out of the retaining ring groove 228 by moving hooks 810 and 812 in a circumferentially opposing manner in directions labeled "$C_1$" and "$C_2$".

Biasing the retaining ring may be enhanced or accomplished by utilizing a removal tool 820. The removal tool 820 is similar to pliers except that the tool 820 has jaws 822 and 824, which are adapted to engage openings 826 and 828 in hooks 810 and 812, respectively and that when the handles are squeezed, the jaws open rather than close. Such a tool is commonly available from medical instrument suppliers. Operating the removal tool 820 when jaws 822 and 824 are inserted into openings 826 and 828 will cause the retaining ring 238 to open and move into its biased position, thereby facilitating removal of vascular tissue connector 116.

Figure 9:
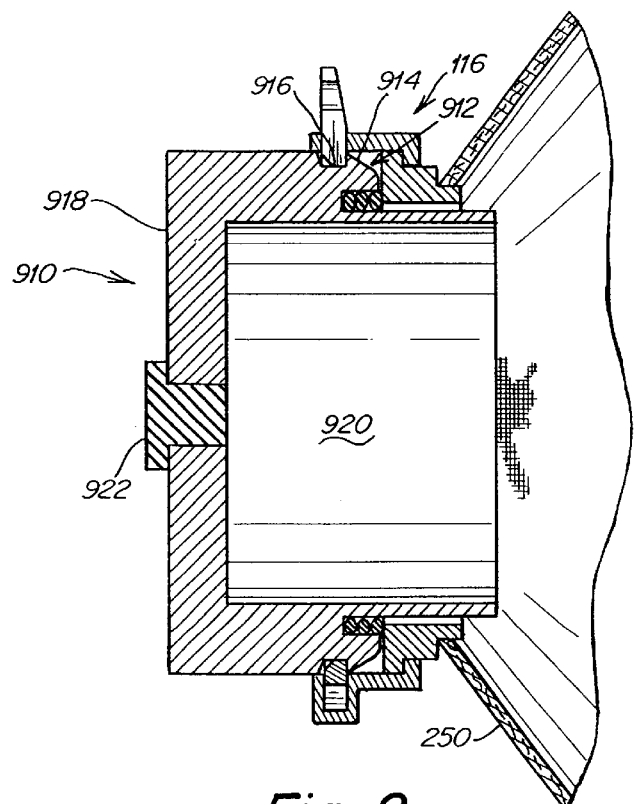
FIG. 9 is a cross-sectional assembly view of a plug connector for use with the connector of FIG. 1; and, FIG. 10 is a cross-sectional view of another connector according to the present invention.

Turning now to FIG. 9, the vascular tissue connector 116 may be coupled to a plug connector 910. Typically, in a surgical procedure, the vascular tissue, such as a blood vessel, is clamped to prevent blood flow out of the blood vessel. The tissue connection member is then sutured to the blood vessel. In order to determine whether or not the sutures between the tissue connection member and the blood vessel leaks, the plug connector 910 is connected to the vascular tissue connector 116 and the surgical clamp is released to increase the blood pressure near the sutures.

Thus, according to the present invention, the plug connector 910 is similar to the base connector 112 in that it is able to connect to the vascular tissue connector 116. In particular, the plug connector 910 is formed with a leading edge 912, having a chamfered portion 914, and a retaining ring groove 916. However, rather than allowing blood to flow therefrom, the plug connector 910 includes an end wall 918 to define a chamber 920. The chamber collects the blood from the blood vessel after the clamp is released.

Alternatively, the plug connector 910 may include a pressure port 922 formed in the end wall 918 leading into the chamber 920. Thus, rather than releasing the clamp on the blood vessel to increase the pressure, a solution, such as saline, may be injected through the pressure port 922, thereby building pressure in the chamber 920 to check the integrity of the sutures between the tissue connection member and the vascular tissue. Removal of the plug connector 910 may be facilitated, as previously discussed with reference to the removal of the vascular connector 116, with the use of the removal tool 820. Once it is determined that the sutures are sound, connection between the base connector 112 and vascular tissue connector 116 may then be accomplished to complete the connection.

Figure 10:
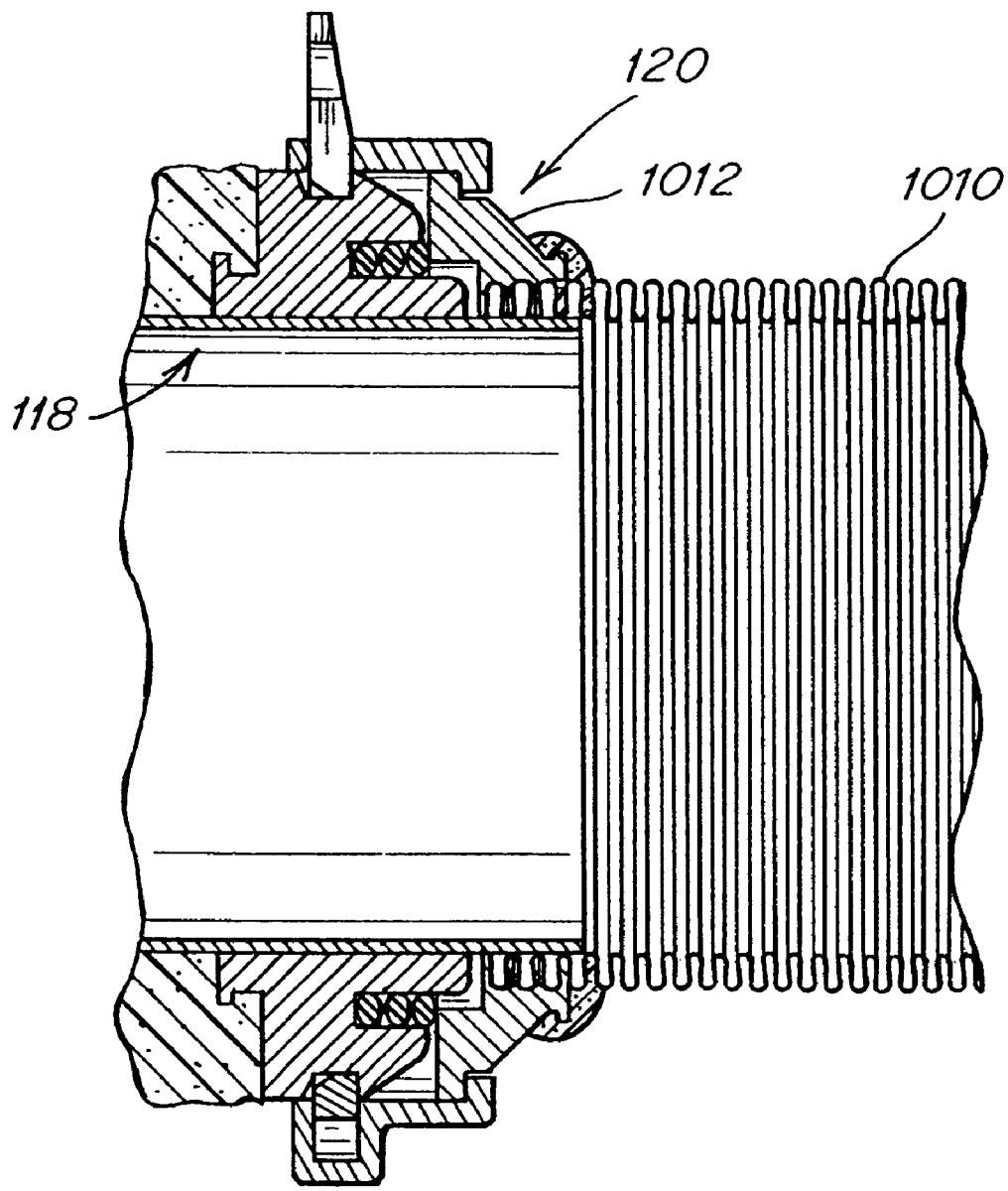

As illustrated in FIG. 1, the cardiac assist device 114 includes two blood flow conduits 140, 142, which are to be connected directly to a patient's vascular system. Base connector 112 and vascular tissue connector 116 are connected to blood flow conduit 140. The second base connector 118 and the second vascular tissue connector 120 are connected to blood flow conduit 142. Although the foregoing detailed description specifically referred to the base connector 112 and the vascular tissue connector 116, it is to be appreciated that the features and function described also relates to the second base connector 118 and the second vascular tissue connector 120. This being said, the difference between lies in the adaptation of the vascular tissue connector being configured to be sutured to either the heart chamber or to a blood vessel. As shown in FIG. 2, when the vascular tissue connector is configured to be sutured to the heart chamber, an atrial cuff 250 is used. The vascular tissue connector 116 thus includes a tissue connection member sleeve 252, which is bonded to atrial cuff 250. As shown in FIG. 10, which illustrates the second connector according to the present invention, when vascular tissue connector is configured to be sutured to a blood vessel, a woven graft 1010 is used. The vascular tissue connector 120 includes a tissue connection member sleeve 1012, which is bonded to woven graft 1010. In either example, the tissue connection member sleeve is held in place by the retaining ring. Also, in either example, when the vascular tissue connector is connected to the base connector, the tissue connection member sleeve compresses the o-ring seals.

In a preferred embodiment, the vascular tissue connector may be supplied as a subassembly. To assemble the vascular tissue connector, the tissue connection member sleeve, together with the tissue connection member (either the atrial cuff 250 or the woven graft 1010), is placed inside of the body of the vascular tissue connector. The retaining ring is then compressed into a biased position (which, for the sake of clarity, is opposite the biased position of the retaining ring when engaging the chamfered portion of the base connector) so as to attain a smaller diameter sufficient to slip into the annular groove formed in the body of the vascular tissue connector. The retaining ring is inserted into the annular groove at a slight angle to allow the hooks to pass through opening formed in the body.

While the best mode for carrying out the invention has been described in detail, those skilled in the art to which this invention relates will recognize various alternative embodiments including those mentioned above as defined by the following claims.

What is claimed is:

1. A medical connector for connecting vascular tissue to a medical device, said connector comprising:

a base connector adapted to be attached to the medical device, with said base connector defining an axis;

a vascular tissue connector defining an axis;

a vascular tissue connection member housed within said vascular tissue connector, said vascular tissue connection member being adapted to connect the vascular tissue connector to vascular tissue;

a retaining ring having a rest position and a biased position, with said retaining ring being housed within a first one of said vascular tissue connector and said base connector;

a retaining ring groove formed on an outer circumference of a second one of said base connector and said vascular tissue connector, with said groove being adapted to engage said retaining ring;

and an alignment feature and an engagement feature each defined by a portion of one of said base connector and said vascular tissue connector and a portion of said retaining ring, with said alignment feature causing said vascular tissue connector to axially self-align with said base connector and with said engagement feature causing said retaining ring to move first into said biased position and then to return at least partially toward the rest position so as to snap into engagement within said retaining ring groove when said vascular tissue connector attaches to said base connector in an axially oriented motion.

2. The connector according to claim 1 wherein said retaining ring comprises a beveled edge, with said beveled edge defining at least a portion of said alignment feature.

3. The connector according to claim 1 wherein one of said base connector and said vascular tissue connector comprises a leading edge defining at least a portion of said alignment feature, with said leading edge comprising a radiused edge and a chamfered portion conjoined with and extending away from said radiused edge.

4. The connector according to claim 3 wherein said retaining ring groove is formed adjacent said chamfered portion.

5. The connector according to claim 1 wherein a portion of said retaining ring is exposed through one of said vascular tissue connector and said base connector so that said retaining ring can be moved to said biased position to facilitate removal of said vascular tissue connector from said base connector.

6. The connector according to claim 1 wherein said retaining ring is in said rest position when said retaining ring is engaged within said retaining ring groove.

7. The connector according to claim 1 wherein one of said vascular tissue connector and said base connector comprises an annular body having an end face, with said end face being completely continuous, thereby reducing tissue snagging when said vascular tissue connector is brought into proximity with said base connector.

8. The connector according to claim 1 wherein one of said vascular tissue connector and said base connector comprises an annular body having an inner and outer surface, with said inner surface having an annular groove formed therein for housing said retaining ring, with said outer surface having an opening formed therein extending through to said annular groove of said inner surface to allow a portion of said retaining ring through said body.

9. The connector according to claim 1 further comprising a plurality of o-ring seals disposed at an interface between said base connector and said vascular tissue connector when connected theretogether, with said interface defining an o-ring seal groove for receiving said o-ring seals in a generally co-axial alignment.

10. The connector according to claim 9 wherein an o-ring seal extends past said o-ring seal groove a predetermined distance.

11. The connector according to claim 10 wherein said predetermined distance is defined by about one-half a diameter of said o-ring seal.

12. The connector according to claim 1 wherein said base connector and said vascular tissue connector each have a body, with each said body having a substantially minimal profile relative to the vascular tissue.

13. The connector according to claim 1 in combination with the medical device.

14. The connector according to claim 1 further comprising a plug connector adapted to be connected to said vascular tissue connector, with said plug connector plugging the vascular tissue when said plug connector is attached to said vascular tissue connector, to test for leakage between said vascular tissue connector and the vascular tissue when said vascular tissue connector is attached to the vascular tissue.

15. The connector according to claim 14 wherein said plug connector includes a pressure port formed therein.

16. A medical connector for connecting a blood vessel to a cardiac assist device, said connector comprising:

a base connector adapted to be connected to the cardiac assist device, with said base connector comprising:
an annular body defining an axis, with said body having a substantially minimal profile relative to a blood vessel to be connected;
a leading edge formed on said body comprising a radiused edge and a chamfered portion conjoined with and extending away from said radiused edge;
an o-ring seal groove formed in said body adjacent said radiused edge;
a plurality of o-ring seals disposed in said o-ring seal groove in substantially coaxial alignment, with an o-ring extending past said o-ring seal groove a predetermined distance; and,
a retaining ring groove formed on an outer circumference of said body adjacent said chamfered portion; and, a vascular tissue connector adapted to be attached to the vascular tissue, with said vascular tissue comprising:
an annular body defining an axis, with said body having a substantially minimal profile relative to the vascular tissue connector;
an end face formed on said body, with said end face being completely continuous, thereby reducing tissue snagging when said vascular tissue connector is brought into contact with said base connector;
a retaining ring housed in said body, with said retaining ring having a rest position and a biased position and further having a beveled edge adjacent said end face, with said beveled edge cooperating with said leading edge of said base connector to axially self-align said vascular tissue connector with said base connector and causing said retaining ring to move first into said biased position and then to snap into engagement with said annular groove when said vascular tissue connector attaches to said base connector in an axially oriented motion; inner and outer surfaces defined by said annular body;
an annular groove formed in said inner surface for housing said retaining ring;
an opening extending from said outer surface through to said annular groove of said inner surface to allow a portion of said retaining ring through said body to facilitate removal of said vascular tissue connector from said base connector; and
a tissue connection member housed within said body, with said tissue connection member being adapted to be attached to the vascular tissue.

17. The connector according to claim 16 in combination with the cardiac assist device.

18. A method of attaching a vascular tissue to a medical device utilizing a medical connector system having at least two connectors; each connector comprising:
   a vascular tissue connector half adapted to mate with the vascular tissue having a longitudinal axis, and an engaging end; and
   a medical device connector adapted to mate with the medical device half having a longitudinal axis, and an engaging end;
      wherein a first one of the vascular tissue and medical device connector halves includes a resilient annular engagement member defining a nominal diameter and a second one of the vascular tissue and medical device connector halves including a leading portion proximate the engaging end, and an annular engagement member receiving element adjacent to the leading portion
      whereby when the longitudinal axes of vascular tissue and medical device connector halves are brought into substantial alignment and their engaging ends moved axially toward one another, the leading portion deflects the resilient annular engagement member away from its nominal diameter to allow engagement of the connector halves, and, when the resilient annular engagement member reaches the annular engagement member receiving element, the resilient annular engagement member snaps back toward its nominal diameter to thereby create a locking engagement between the connector halves and provide a surgeon operating the connector with tactile feed back that a locking engagement has been made; the method comprising the steps of:
   suturing a first vascular tissue connector half, to a first vascular tissue;
   positioning the medical device such that a first medical device connector half aligns with the first vascular tissue connector to determine the required length of a second vascular tissue connection half;
   conforming the second vascular tissue connection half to the determined length;
   sewing the second vascular tissue connection half to a second vascular tissue;
   positioning the medical device such that both medical device connector halves align with both vascular tissue connectors, respectively; and,
   axially moving each medical device connector half relative to each vascular tissue connector half in an axial direction until tactile feedback of locking engagement is detected.

19. The method according to claim 18 wherein the connector system further includes a plug connector having engagement features substantially similar to a medical device connector half, with said method further comprising the steps of:
   connecting the plug connector to the vascular tissue connector half thereby plugging the vascular tissue; and,
   testing for leakage between the vascular tissue connector half and the vascular tissue.

20. The method according to claim 19 wherein said testing step comprises the step of releasing a clamp from the vascular tissue to allow blood pressure to build in the vascular tissue connector half.

21. The method according to claim 19 wherein the plug connector includes a pressure port and wherein said testing step includes the step of injecting a solution through the pressure port thereby causing pressure to build in the vascular tissue connector half.

22. The method according to claim 19 wherein the connector system further includes a removal tool, with said method further comprising the step of removing one of said vascular tissue connector halves and said plug connector with the removal tool.

23. The method according to claim 18 wherein the connector system further includes an installation tool, wherein said axially pushing step comprises the step of holding the vascular tissue connector half with the installation tool.

24. The method of claim 18, wherein each connector further comprises a resilient annular sealing element disposed on a first one of the vascular tissue and medical device connector halves and facing in an axial direction toward a second one of the first and second connector halves when the longitudinal axes of the first and second connector halves are aligned, the resilient sealing element biasing the connector halves axially against engagement.

25. A medical quick connector for connecting vascular tissue to a medical device, the connector comprising:
   a first connector half having a longitudinal axis, an engaging end, and a resilient annular engagement member defining a nominal diameter;
   a second connector half having a longitudinal axis, an engaging end, a leading portion proximate the engaging end, and an annular engagement member receiving element adjacent to the leading portion; and
   a resilient annular sealing element disposed on a first one of the first and second connector halves and facing in an axial direction toward a second one of the first and second connector halves when the longitudinal axes of the first and second connector halves are aligned, the resilient sealing element biasing the connector halves axially against engagement;
      wherein a first one of the first and second connector halves is adapted to mate with the vascular tissue and a second one of the first and second connector halves is adapted to mate with the medical device; and
      whereby when the longitudinal axes of first and second connector halves are brought into substantial alignment and their engaging ends moved axially toward one another, the leading portion of the second connector half deflects the resilient annular engagement member away from its nominal diameter to allow engagement of the connector halves, and, when the resilient annular engagement member reaches the annular engagement member receiving element, the resilient annular engagement member snaps back toward its nominal diameter to thereby create a locking engagement between the connector halves.

26. The connector of claim 25, wherein the resilient annular sealing element comprises at least one resilient O-ring disposed in an annular O-ring groove formed in the first one of the first and second connector halves.

27. The connector of claim 26, wherein the resilient annular sealing element comprises a plurality of O-rings disposed in the O-ring groove.

28. The connector of claim 26, wherein the O-ring groove faces in an axial direction and towards a second one of the first and second connector halves when the first and second connector halves are axially aligned for engagement.

29. The connector of claim 26, wherein the O-ring groove is disposed toward the engagement end from the resilient annular locking element or the annular engagement member receiving element.

30. The connector of claim 25, wherein the resilient annular engagement member comprises a circular snap ring and the annular engagement member receiving element comprises a groove.

31. The connector of claim 30, wherein the snap ring has a groove mating surface substantially transverse to the longitudinal axis and facing in a direction opposite to the engaging end, and the groove has an opposed ring mating surface substantially transverse to the longitudinal axis and facing in a direction opposite to the engaging end.

32. The connector of claim 31, wherein the snap ring includes a means for deflecting the snap ring away from the nominal diameter to allow disengagement of the connector halves.

33. The connector according to claim 30 wherein the snap ring comprises a beveled leading edge.

34. The connector according to claim 30 wherein a portion of the snap ring is exposed through one of the first and second connector halves so that the retaining ring can be moved to the biased position to facilitate removal of the vascular tissue connector from the base connector.

35. The connector according to claim 30 wherein the snap ring is in the rest position when the snap ring is engaged with the groove.

36. The connector of claim 25, further comprising means for pressure testing a connection between a connector half and vascular tissue.

37. The connector according to claim 25 wherein one of the first and second connector halves comprises a leading edge defining at least a portion of a self alignment feature, with the leading edge comprising a radiused edge and a chamfered portion conjoined with and extending away from the radiused edge.

38. The connector according to claim 25 wherein one of the first and second connector halves comprises an annular body having an end face, the end face being completely continuous, thereby reducing tissue snagging when the first connector half is brought into proximity with the second connector half.

39. A self-aligning medical quick connector system connecting vascular tissue to a medical device, the connector system comprising:
    a male connector having a longitudinal axis and an engaging end;
    a female connector having a longitudinal axis and an engaging end;
    a locking engagement means provided on a first one of the male and female connectors for creating an axial locking engagement between the male and female connectors;
    an engagement receiving means provided on a second one of the male and female connectors for cooperating with the engagement means to create an axial locking engagement between the male and female connectors; and
    an alignment means comprising a taper provided on the male connector tapering inward toward the longitudinal axis in a direction toward the engaging end, and having a radiused edge adjacent the engaging end and a chamfer formed on the locking engaging means in a direction corresponding to the direction of the taper of the male connector;
        whereby when the male and female connectors are brought into engagement, the alignment means engages the female connector to cause the longitudinal axes of the male and female connectors to align, followed by a locking engagement between the locking engagement means.

40. The connector system of claim 39, wherein the locking engagement means comprises a resilient annular engagement member defining a nominal diameter disposed on the female connector proximate to the engaging end, the annular engagement member deflecting so as to have a diameter greater than the nominal diameter in response to contact with the male connector, the annular engagement member further causing axial alignment of the male and female connectors.

41. The connector system of claim 40, wherein the engagement receiving means comprises an annular engagement member receiving groove disposed on the male connector on an opposite side of the taper from the engaging end and, upon engagement of the male and female connectors, the annular engagement member deflects outward from its nominal diameter in response to contact from the taper on the male connector, the annular engagement member snapping back toward its nominal diameter upon engagement with the annular engagement member receiving groove to thereby create a locking engagement between the male and female connectors and provide a surgeon operating the connectors with tactile feed back that a locking engagement has been made.

42. A medical quick connector system connecting vascular tissue to a medical device, the connector comprising:
    a male connector having a longitudinal axis and an engaging end;
    a female connector having a longitudinal axis and an engaging end;
    a locking engagement means provided on a first one of the male and female connectors for creating an axial locking engagement between the male and female connectors;
    an engagement receiving means provided on a second one of the male and female connectors for cooperating with the engagement means to create an axial locking engagement between the male and female connectors; and
    a means for preventing tissue snagging during engagement of the connectors;
        whereby when the male and female connectors are brought into axial alignment and engaged, the locking engagement means engages the engagement receiving means to create a locking engagement between the male and female connectors without tissue snagging.

43. The connector system of claim 42, wherein the means for preventing tissue snagging comprises a completely continuous end face provided at the engaging end of the female connector.

44. A medical quick connector for connecting vascular tissue to a medical device, the connector comprising:
    a vascular tissue connector half adapted to mate with the vascular tissue having a longitudinal axis, and an engaging end;
    a medical device connector half adapted to mate with the medical device having a longitudinal axis, and an engaging end;
    wherein a first one of the vascular tissue and medical device connector halves includes a resilient annular engagement member defining a nominal diameter and a second one of the vascular tissue and medical device connector halves including a leading portion proximate the engaging end, and an annular engagement member receiving element adjacent to the leading portion; and a pressure testing means having engagement features substantially similar to the medical device connector, the pressure testing means being replaceably engageable with the vascular tissue connector half to pressure test a mating connection between the vascular tissue connector half and the vascular tissue;

whereby when the longitudinal axes of vascular tissue and medical device connector halves are brought into substantial alignment and their engaging ends moved axially toward one another, the leading portion deflects the resilient annular engagement member away from its nominal diameter to allow engagement of the connector halves, and, when the resilient annular engagement member reaches the annular engagement member receiving element, the resilient annular engagement member snaps back toward its nominal diameter to thereby create a locking engagement between the connector halves.

45. A medical connector for connecting vascular tissue to a medical device, the connector comprising:

a base connector adapted to be attached to the medical device, with the base connector defining an axis;

a vascular tissue connector adapted to be attached to the vascular tissue, with the vascular tissue connector defining an axis;

a retaining ring having a rest position and a biased position, with the retaining ring being housed within a first one of the vascular tissue connector and the base connector;

a retaining ring groove formed on an outer circumference of a second one of the base connector and the vascular tissue connector, with the groove being adapted to engage the retaining ring;

and an alignment feature and an engagement feature each defined by a portion of one of the base connector and the vascular tissue connector and a portion of the retaining ring, with the alignment feature causing the vascular tissue connector to axially self-align with the base connector and with the engagement feature causing the retaining ring to move first into the biased position and then to return at least partially toward the rest position so as to snap into engagement within the retaining ring groove when the vascular tissue connector attaches to the base connector in an axially oriented motion, the alignment feature comprising a beveled leading edge on the retaining ring.

46. The connector according to claim 45 wherein one of the base connector and the vascular tissue connector comprises a leading edge defining at least a portion of the alignment feature, with the leading edge comprising a radiused edge and a chamfered portion conjoined with and extending away from the radiused edge.

47. The connector according to claim 45 wherein a portion of the retaining ring is exposed through one of the vascular tissue connector and the base connector so that the retaining ring can be moved to the biased position to facilitate removal of the vascular tissue connector from the base connector.

48. The connector according to claim 45 wherein the retaining ring is in the rest position when the retaining ring is engaged with the retaining ring groove.

49. The connector according to claim 45 wherein one of the vascular tissue connector and the base connector comprises an annular body having an end face, with the end face being completely continuous, thereby reducing tissue snagging when the vascular tissue connector is brought into proximity with the base connector.

50. The connector according to claim 45 wherein one of the vascular tissue connector and the base connector comprises an annular body having an inner and outer surface, with the inner surface having an annular groove formed therein for housing the retaining ring, with the outer surface having an opening formed therein extending through to the annular groove of the inner surface to allow a portion of the retaining ring through the body.

51. The connector according to claim 45 further comprising a plurality of o-ring seals disposed at an interface between the base connector and the vascular tissue connector when connected theretogether, with the interface defining an o-ring seal groove for receiving the o-ring seals in a generally co-axial alignment.

52. The connector according to claim 51 wherein an o-ring seal extends past the o-ring seal groove a predetermined distance.

53. The connector according to claim 52 wherein the predetermined distance is defined by about one-half a diameter of the o-ring seal.

54. The connector according to claim 45 further comprising a tissue connection member housed within the vascular tissue connector, with the tissue connection member being adapted to be attached to the vascular tissue.

55. The connector according to claim 45 wherein the base connector and the vascular tissue connector each have a body, with each body having a substantially minimal profile relative to the vascular tissue.

56. The connector according to claim 45 in combination with the medical device.

57. The connector according to claim 45 further comprising a plug connector adapted to be connected to the vascular tissue connector, with the plug connector plugging the vascular tissue when the plug connector is attached to the vascular tissue connector, to test for leakage between the vascular tissue connector and the vascular tissue when the vascular tissue connector is attached to the vascular tissue.

58. The connector according to claim 57 wherein the plug connector includes a pressure port formed therein.

59. A medical quick connector for connecting vascular tissue to a medical device, the connector comprising:

a vascular tissue connector half adapted to mate with the vascular tissue and having a longitudinal axis, and an engaging end;

a medical device connector half adapted to mate with the medical device and having a longitudinal axis, and an engaging end;

wherein a first one of the vascular tissue and medical device connector halves includes a resilient annular engagement member defining a nominal diameter and a second one of the vascular tissue and medical device connector halves including a leading portion proximate the engaging end, and an annular engagement member receiving element adjacent to the leading portion; and a plug connector adapted to be connected to the vascular tissue connector and having engagement features, the plug connector being replaceably engageable with the vascular tissue connector half to pressure test a mating connection between the vascular tissue connector and the vascular tissue.

60. The connector according to claim 59 wherein one of the medical device connector half and the vascular tissue connector half comprises a leading edge defining at least a portion of the alignment feature, with the leading edge comprising a radiused edge and a chamfered portion conjoined with and extending away from the radiused edge.

61. The connector according to claim 59 wherein a portion of the annular engagement member is exposed through one of the vascular tissue connector half and the medical device connector half so as to facilitate removal of the vascular tissue connector half from the medical device connector half.

62. The connector according to claim 59 wherein one of the vascular tissue connector half and the medical device connector half comprises an annular body having an end face, with the end face being completely continuous, thereby reducing tissue snagging when the vascular tissue connector half is brought into proximity with the medical device connector half.

63. The connector according to claim 59 further comprising at least one o-ring seal disposed at an interface between the medical device connector half and the vascular tissue connector half when connected theretogether, with the interface defining an o-ring seal groove for receiving the at least one o-ring seal in a generally co-axial alignment.

64. The connector according to claim 63 wherein an o-ring seal extends past the o-ring seal groove a predetermined distance.

65. The connector according to claim 64 wherein the predetermined distance is defined by about one-half a diameter of the o-ring seal.

66. The connector according to claim 63 wherein the at least one o-ring seal consists of a plurality of o-ring seals.

67. The connector according to claim 59 further comprising a tissue connection member housed within the vascular tissue connector half, with the tissue connection member being adapted to be attached to the vascular tissue.

68. The connector according to claim 59 wherein the medical device connector half and the vascular tissue connector half each have a body, with each body having a substantially minimal profile relative to the vascular tissue.

69. A medical connector for connecting vascular tissue to a medical device, said connector comprising:
   a base connector adapted to be attached to the medical device, with said base connector defining an axis;
   a vascular tissue connector adapted to be attached to the vascular tissue, with said vascular tissue connector defining an axis;
   a retaining ring having a rest position and a biased position, with said retaining ring being housed within a first one of said vascular tissue connector and said base connector;
   a retaining ring groove formed on an outer circumference of a second one of said base connector and said vascular tissue connector, with said groove being adapted to engage said retaining ring; and
   an alignment feature and an engagement feature each defined by a portion of one of said base connector and said vascular tissue connector and a portion of said retaining ring, with said alignment feature causing said vascular tissue connector to axially self-align with said base connector and with said engagement feature causing said retaining ring to move first into said biased position and then to return at least partially toward the rest position so as to snap into engagement within said retaining ring groove when said vascular tissue connector attaches to said base connector in an axially oriented motion wherein one of said vascular tissue connector and said base connector comprises an annular body having an end face, with said end face being completely continuous, thereby reducing tissue snagging when said vascular tissue connector is brought into proximity with said base connector.

70. The connector according to claim 69 wherein one of the base connector and the vascular tissue connector comprises a leading edge defining at least a portion of the alignment feature, with the leading edge comprising a radiused edge and a chamfered portion conjoined with and extending away from the radiused edge.

71. The connector according to claim 69 wherein a portion of the retaining ring is exposed through one of the vascular tissue connector and the base connector so that the retaining ring can be moved to the biased position to facilitate removal of the vascular tissue connector from the base connector.

72. The connector according to claim 69 wherein the retaining ring is in the rest position when the retaining ring is engaged with the retaining ring groove.

73. The connector according to claim 69 wherein one of the vascular tissue connector and the base connector comprises an annular body having an inner and outer surface, with the inner surface having an annular groove formed therein for housing the retaining ring, with the outer surface having an opening formed therein extending through to the annular groove of the inner surface to allow a portion of the retaining ring through the body.

74. The connector according to claim 69 further comprising at least one o-ring seal disposed at an interface between the base connector and the vascular tissue connector when connected theretogether, with the interface defining an o-ring seal groove for receiving the at least one o-ring seal in a generally co-axial alignment.

75. The connector according to claim 69 wherein the at least one o-ring seal consists of a plurality of o-ring seals.

76. The connector according to claim 74 wherein an o-ring seal extends past the o-ring seal groove a predetermined distance.

77. The connector according to claim 76 wherein the predetermined distance is defined by about one-half a diameter of the o-ring seal.

78. The connector according to claim 69 further comprising a tissue connection member housed within the vascular tissue connector, with the tissue connection member being adapted to be attached to the vascular tissue.

79. The connector according to claim 69, wherein the base connector and the vascular tissue connector each have a body, with each body having a substantially minimal profile relative to the vascular tissue.

80. The connector according to claim 69 in combination with the medical device.

81. The connector according to claim 69 further comprising a plug connector adapted to be connected to the vascular tissue connector, with the plug connector plugging the vascular tissue when the plug connector is attached to the vascular tissue connector, to test for leakage between the vascular tissue connector and the vascular tissue when the vascular tissue connector is attached to the vascular tissue.

82. The connector according to claim 81 wherein the plug connector includes a pressure port formed therein.

* * * * *

UNITED STATES PATENT AND TRADEMARK OFFICE
CERTIFICATE OF CORRECTION

PATENT NO. : 6,319,231 B1
DATED : November 20, 2001
INVENTOR(S) : Andrulitis

It is certified that error appears in the above-identified patent and that said Letters Patent is hereby corrected as shown below:

Column 18,
Line 35, replace "69" with -- 74 --

Signed and Sealed this

Twelfth Day of November, 2002

*Attest:*

*Attesting Officer*

JAMES E. ROGAN
*Director of the United States Patent and Trademark Office*